(12) United States Patent
Dvorak et al.

(10) Patent No.: US 10,181,011 B2
(45) Date of Patent: Jan. 15, 2019

(54) HEALTHCARE INFORMATION SYSTEM WITH CLINICAL INFORMATION EXCHANGE

(71) Applicant: EPIC SYSTEMS CORPORATION, Verona, WI (US)

(72) Inventors: Carl Dvorak, Madison, WI (US); Khiang Seow, Madison, WI (US); Charles Young, Palo Alto, CA (US)

(73) Assignee: EPIC SYSTEMS CORPORATION, Verona, WI (US)

( * ) Notice: Subject to any disclaimer, the term of this patent is extended or adjusted under 35 U.S.C. 154(b) by 0 days.

(21) Appl. No.: 15/131,738

(22) Filed: Apr. 18, 2016

(65) Prior Publication Data
US 2016/0232305 A1    Aug. 11, 2016

Related U.S. Application Data

(63) Continuation of application No. 13/220,141, filed on Aug. 29, 2011, which is a continuation of application No. 10/052,659, filed on Jan. 18, 2002.

(51) Int. Cl.
*G16H 15/00* (2018.01)
*G06F 19/00* (2018.01)
(Continued)

(52) U.S. Cl.
CPC ............ *G06F 19/322* (2013.01); *G06F 11/30* (2013.01); *G06F 19/3418* (2013.01);
(Continued)

(58) Field of Classification Search
CPC .......... G06F 19/32; G06F 19/34; G06F 11/34; G06Q 50/22; G06Q 50/24
See application file for complete search history.

(56) References Cited

U.S. PATENT DOCUMENTS

| | | | | |
|---|---|---|---|---|
| 5,890,129 A | * | 3/1999 | Spurgeon | B42D 15/00 705/2 |
| 6,718,489 B1 | * | 4/2004 | Lee | G06F 11/0748 714/43 |

(Continued)

OTHER PUBLICATIONS

C. Simache ; M. Kaaniche ; A. Saidane; "Event log based dependability analysis of Windows NT and 2Ksystems;" 2002 Pacific Rim International Symposium on Dependable Computing, 2002. Proceedings, pp. 311-315. (Year: 2002).*

*Primary Examiner* — Rachel L. Porter
(74) *Attorney, Agent, or Firm* — Quarles & Brady LLP

(57) ABSTRACT

In a system for distributed computing in a health care environment in which multiple different applications are in use connected on a common computer network, the improvement comprising at least one clinical exchange server on the network, the clinical exchange server including memory, the clinical exchange server programmed to perform the steps of (i) maintaining a separate patient record for each of a plurality of patients wherein each patient record includes an event registry including separate event data subsets for each event recorded by any of the different applications where each event data subset indicates the application that recorded the event and event summary data wherein the event summary data is less than all of the data recorded by the application that recorded the event, (ii) receiving a first query from the first application for patient information associated with a first patient where the first query includes information usable to identify an event in the event registry, (iii) using the information in the first query and the event data subsets in the event registry to identify an event in the event registry associated with the first query, the event identified being an identified event, (iv) identifying an application that recorded the identified event from the event data subset associated with the identified event, the appli- (Continued)

cation identified being an identified application, (v) generating a second query that specifies the identified event, and (vi) transmitting the second query to the identified application.

20 Claims, 4 Drawing Sheets

(51) Int. Cl.
| | | |
|---|---|---|
| G06F 11/30 | (2006.01) | |
| G06Q 50/22 | (2018.01) | |
| G06Q 50/24 | (2012.01) | |
| G16H 10/60 | (2018.01) | |
| G16H 40/20 | (2018.01) | |

(52) U.S. Cl.
CPC ............. *G06Q 50/22* (2013.01); *G06Q 50/24* (2013.01); *G16H 10/60* (2018.01); *G16H 40/20* (2018.01); *G06F 19/328* (2013.01)

(56) References Cited

U.S. PATENT DOCUMENTS

| | | | |
|---|---|---|---|
| 6,757,898 B1 * | 6/2004 | Ilsen | G06F 19/324 |
| | | | 600/300 |
| 7,017,161 B1 * | 3/2006 | Cyr | G06F 9/544 |
| | | | 705/2 |
| 2002/0035488 A1 * | 3/2002 | Aquila | G06Q 40/02 |
| | | | 705/4 |

* cited by examiner

HEALTHCARE INFORMATION SYSTEM WITH CLINICAL INFORMATION EXCHANGE

CROSS-REFERENCE TO RELATED APPLICATIONS

This application is a continuation of U.S. patent application Ser. No. 13/220,141, filed on Aug. 29, 2011, which is a continuation of Ser. No. 10/052,659, U.S. patent application Ser. No. filed Jan. 18, 2002, which are incorporated herein by reference in their entirety.

STATEMENT REGARDING FEDERALLY SPONSORED RESEARCH OR DEVELOPMENT

Not applicable.

BACKGROUND OF THE INVENTION

Most health care institutions make extensive use of computers for record keeping and patient service. In fact, most health care providers rely on more than on type of computerized system. Typically providers of computerized systems for health care providers have tended to focus on one or more aspects of the total automation needs of health care providers and thus there are often at a single health care institution separate computer systems for billing and accounting, laboratory, in- or out-patient scheduling or tracking, medical records, appointments and others. Some such different systems may be different software packages while others may involve entirely different computer hardware systems as well. In some cases, all systems in an organization are linked by a network, but such a network connection alone does not ensure that the systems can cooperatively exchange information among the divergent systems in the network. Often the different systems communicate by way of one or more software interfaces that must be custom built for each pair of systems which must communicate, even on the same network. It is also a trend in the health care industry in general that different organizations can cross-refer or partner in one or more areas or for certain types of patients, and thus different organizations with entirely different computer systems and networks find a need to share patient data.

An emerging driving application for computerization in healthcare is electronic medical records. Completely computerized medical records can dramatically assist in the intelligence of health care service delivery to patients. However, to be completely effective, the prompt sharing of critical patient information amongst the caregivers who might treat a particular patient becomes important. This needs extends both within a large health care organization as well as to allied health care providers, such as referral sources in outside organizations, who may refer in patients and who already possess significant clinical information about the patients. This need also arises in the exchange of information between distinct healthcare organizations, whether operating similar or dissimilar computer systems, who are also called on from time to time to efficiently exchange information about patients who need treatment at other institutions. There are no standards widely in use at this time to facilitate the exchange or dissemination of clinical or other information of this type.

BRIEF SUMMARY OF THE INVENTION

The present invention is summarized in that a system for distributed computing in a health care environment in which multiple different applications are in use, connected on a common computer network, there is a clinical exchange server on the network, the clinical exchange server including memory, the clinical exchange server programmed to maintain a reference table, the reference table including a list of applications on the network and information about the patient identification number used by each application, to maintain a list of events reported to it by other applications on the network and to respond to inquiries from a first application about an event recorded by a second application by transmitting a query to the second application based on the information in the reference table and the list of reported events.

The present invention is intended to provide a flexible system of permitting the exchange of clinical data among disparate computer systems either in a common healthcare enterprise or between enterprises.

The present system is intended to permit a standard protocol for information exchange among computer systems collecting clinical data about patient in a simple protocol intended to minimize overhead.

A clinical exchange server in accordance with the present invention has as one of its advantages that it enables an interface for otherwise incompatible computer systems to share data about patients.

Other advantages, features, and objects of the present invention will become apparent from a detailed review of the following specification.

DETAILED DESCRIPTION OF THE INVENTION

Figure 1:
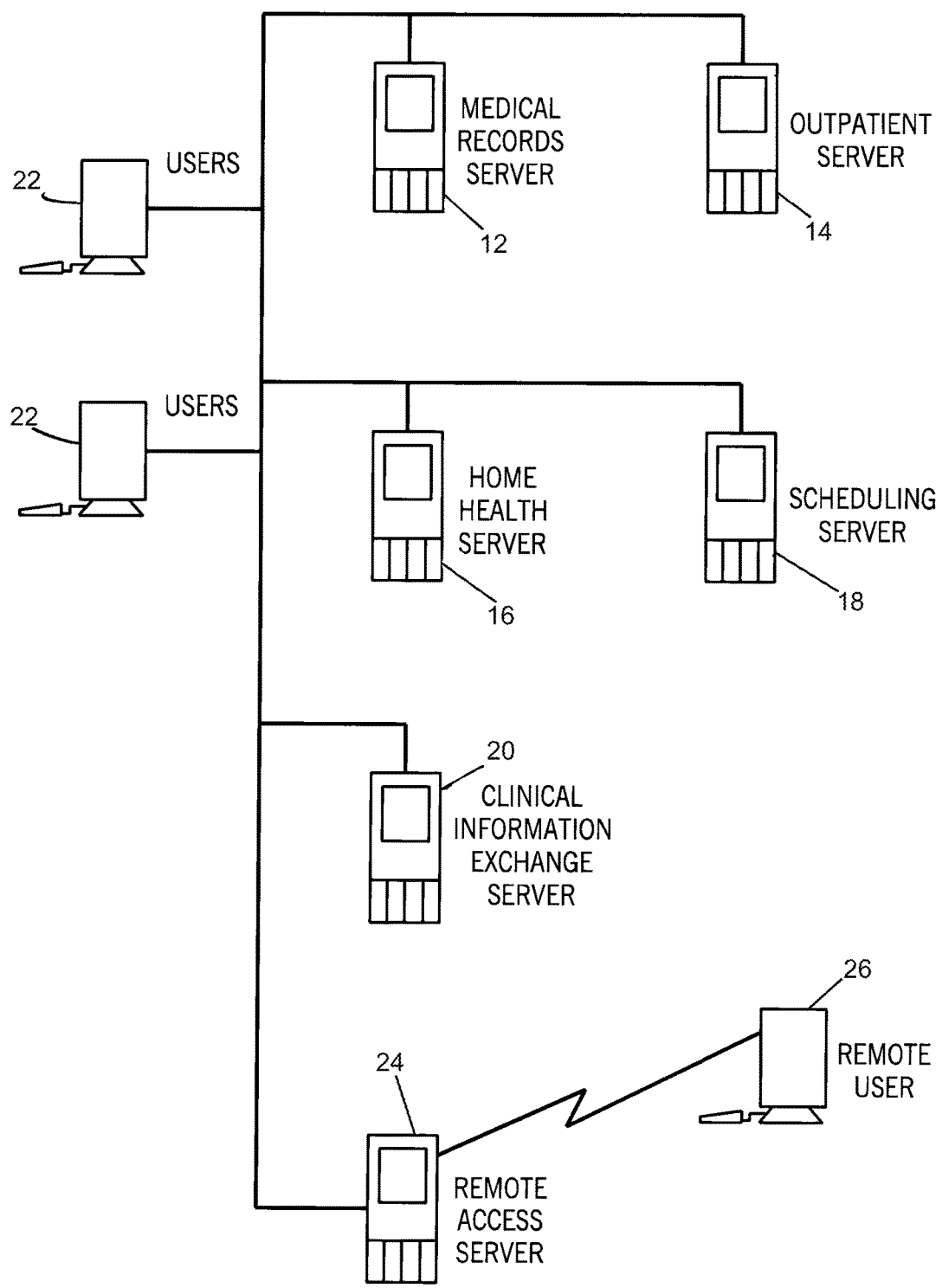
FIG. 1 is schematic diagram of the clinical exchange server of the present invention as integrated into a typical information system for a large health care institution.

The device, system and method described here are intended to facilitate the exchange of information throughout a multifaceted health care enterprise and also between health case enterprises. Modern health care organizations often offer a wide variety of health care services to their patients, including both in-patient and out-patient services as well as a long list of so-called ancillary services such as physical therapy, occupational therapy and home assistance or nursing care. Typically in such organizations, there are a number of different computer software application programs serving different roles such as tracking patients, service, schedules, charges or medical results or records. Often the different applications are from different vendors who each specialize in a given sector or service within the environment, such as in-patient scheduling, laboratory results reporting, or managed care analysis. Often such applications communicate among themselves rather poorly. This invention is intended to enable such an organization or enterprise to exchange certain defined information between applications and throughout the enterprise in a defined manner. The system is based on the use of a clinical information exchange server device, referred to here sometimes by the acronym CIXSD. In brief, the CIXSD is a dedicated server which communicates with the various computer applications operated by the enterprise. The CIXSD serves as a central repository of patient identifying information and serves as a reference point which each different application can interrogate to find out certain defined information about events that have been recorded or tracked by any other application in the enterprise. In this context, the term "event" refers to any category of event or patient encounter tracked or recorded by one of the computer software applications in the enterprise. For example, and event could be a patient treatment encounter, a laboratory report, a chart entry, an accounting entry, or any other data item which is kept by one or another of the various medical information software applications in the enterprise. The CIXSD stores a set of identifying information about the patient and an event registry associated with each patient. The event registry maintains data items for each event, including a minimized set of information about the event and an identification of the system that recorded and maintains a record of the event. In short, the event registry data item includes a categorization of the event and the location and system holding the information about the event, but not detailed data describing the event itself. For example, the event registry typically does not contain actual medical records data but contains instead identifiers that can be used to compose a query to the system maintaining data about the event so that the medical records application about the event on which it holds data.

It is envisioned that for most computerized health care services enterprises, at least one computer server connected to the network for the enterprise will maintain a complete listing of all of the patients who are seen anywhere in the enterprise and patient unique identifiers for each such patient. This listing is referred to here as the Master Patient Index. It is not critical which application system is designated as maintaining the Master Patient Index, and the Master Patient Index can be a centralized or distributed index, as long some mechanism is maintained to list and separately identify all patients. The CIXSD works in cooperation with the Master Patient Index but is not intended to be a replacement for it. Each enterprise using a computer system has, or should have, a Master Patient Index which assigns a system-unique identification code for each unique patient. The CIXSD does not address the issues of matching patients and monitoring access to patient data. The CIXSD creates and maintains an event registry associated with each patient in the Master Patient Index.

Physically the CIXSD may be a distinct dedicated server, or it can be implemented in a server which is also operating other concurrent functions. The CIXSD may also be operated as a subsidiary functions of a system which serves as the Master Patient Index (MPI). While the MPI and CIXSD functions are distinct, since the CIXSD operates on the base of information provided to it by the MPI, the two functions can, if preferred, be operated by a single server. Some functionality needed for the CIXSD can be separately stored by the CIXSD server or can be stored by the MPI with which the CIXSD is associated. For example, the Epic MPI provides an Patient Clinical Event History, which can be used by the CIXSD, but if another MPI does not itself support such a function, the CIXSD can support this function itself. The Patient Clinical Event History is a registry of all important clinical events which have involved a particular patient.

The CIXSD should be a server, in the sense that it maintains a data registry and that it can be accessed by stations throughout the network to which it is connected. THE CIXSD may or may not be a separate server from the server supporting the MPI function. The CIXSD also includes a set of simple protocols designed to allow separate and distinct systems to exchange clinical information on a patient. Using these protocols, described in more detail below, distinct and separate systems can share patient clinical data in a manner that seems seamless to the user. The CIXSD may also be defined by an interface designed to permit transferal of clinical information among systems.

Thus, for purposes of illustration, shown schematically in FIG. 1 is a health care enterprise network of computer systems. In the illustration of FIG. 1, each separate application in the network is resident on a separate server, and all the servers are connected onto a common network. Thus the overall system includes, in this example, a medical records server 12, an outpatient records server 14, a home health server 16, a scheduling server 18 and a clinical information exchange server (CIXSD) 20. Each of the application servers is running the application program which its name implies, i.e. the medical records server is running a medical records program. A plurality of independent users is illustrated by the terminals 22, any of the users at any of the terminals 22 being able to operate any of the applications on any of the servers. A remote access server 24 also supports access by remote users, illustrated by the remoter terminal 26. Each of the servers includes the appropriate computer components including a processor, random access memory and mass storage devices such as magnetic disk or tape drives. The users access each of the systems over the common network, but, in essence, only access any one system at any one time.

It is also envisioned that the hardware arrangement of FIG. 1 is only one of the many ways in which the systems can be physically configured. For example, each system might instead consist of a single processor with a number of dedicated terminals which only interact with that one computer to operate some special software system. Or there may be dedicated networks operating only a single operation which care connected to each other only by specific limited linkages. Whichever configuration is used, the dedicated computers or servers still must communicate in some way with other computers or networks in the enterprise by a communication interface device or software.

The CIXSD is intended to permit each of the applications in the enterprise to learn something about and to access information about patient events stored by other systems in the operation. The CIXSD does not, and is not intended, to store all of the information stored by each application system about the patient event. The CIXSD serves instead as a sort of pointer to direct any given application as to where to find information it may need to access in another application.

Figure 2:
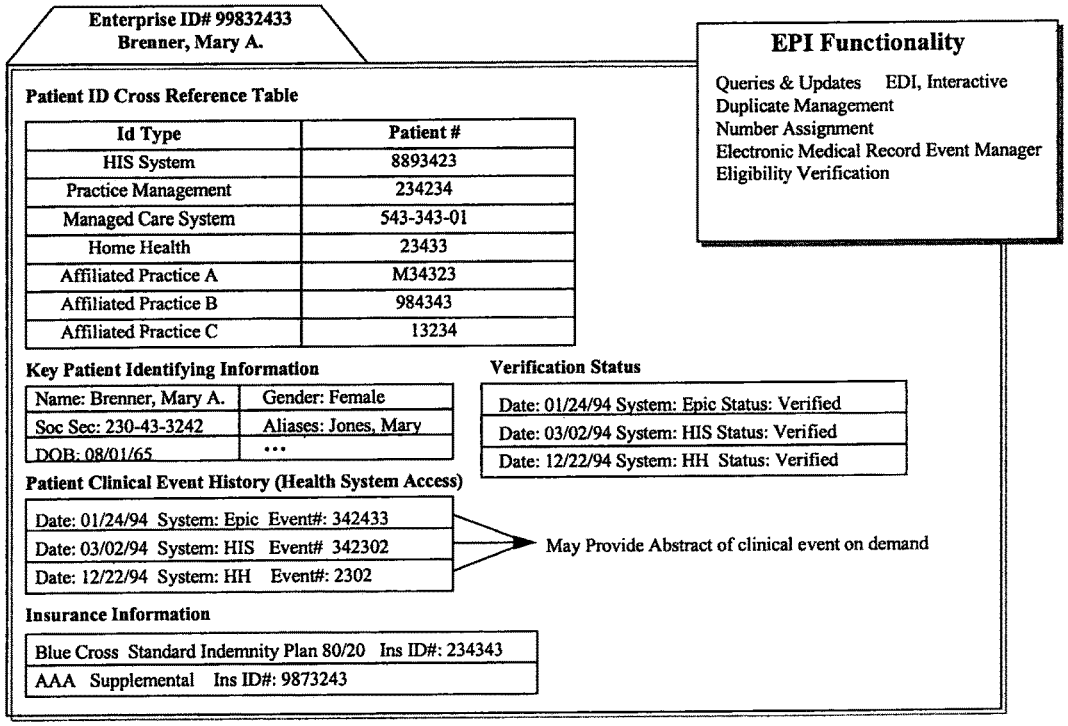
FIG. 2 is an illustration of a data set of items of data that might be captured by a clinical exchange server.

Illustrated in FIG. 2 is an exemplary record for a patient as stored in a Master Patient Index implementing CIXSD. The placement and organization of the data in the illustration of FIG. 2 is, of course, arbitrary, but what is important is the nature of the information maintained by the server device. Referring to FIG. 2, at the top is a data item, "Enterprise ID#99832433" intended to indicate the name and enterprise identification number of the patient in the system hosting the CIXSD. The CIXSD follows the convention of the server designated as the Master Patient Index in assigning the patient identification code to the patient. Immediately below the enterprise identification number is the name of the patient. Below the patient master identification and name is a patient identification cross reference table. This table is a look-up table to facilitate easy look up of the various patient identification numbers or codes assigned by each of the software applications in the enterprise to that identify the same patient. This table includes an identification of the software applications and the patient identification numbers assigned to the patient by each separate software application. It is envisioned that some of the patient identifications will be assigned by diverse applications in the organization originating from different vendors. It is also envisioned that some of the identification codes refer to identification methods used by related organizations or remote medical practices with which the enterprise might, on occasion, share or cross-refer patients. Such entities are often called affiliates, and are referred to as such in FIG. 2. Thus in the table illustrated in FIG. 2, under the column heading "Id Type" is a listing of applications and affiliates and under the column heading "Patient #" is listed the identification number used by that application, or that affiliated facility, for that patient.

As illustrated as well in FIG. 2, the CIXSD data base entry for this patient also includes certain additional identifying information about the patient such as gender, age and the like. This is illustrated in FIG. 2 right underneath the patient identification cross reference table. The CIXSD data base also includes insurance information for the patient, since that information is likely to be needed quickly by many of the applications in the enterprise, and the insurance information is illustrated in the lower left portion of FIG. 2. Finally, the CIXSD record for that patient includes an event registry, shown in part here under the heading "Patient Clinical Event History." The event registry is a summary or abstract of the detail on all events that are kept by any one of the application systems. For each data item in the event registry, the CIXSD will keep a listing of the type of event, the date of the event, the application system holding data about the event and an assigned unique event number. The CIXSD does not attempt to keep a full record of all such events, but just an indication that the event occurred and an indication as to where to find additional information about the event. The indication as to where to find more information is the name of the host application which holds the event from which the event registry has abstracted this information.

The CIXSD can thus serve as an interpreter or intermediary to facilitate data transfer among different applications in the enterprise. The CIXSD can receive a query from a first application system and sent an inquiry from a second application system to permit the first application to recover data it needs to process a request. The billing system might need, for example, data about a procedure performed on a patient. In this instance, the billing application would send an inquiry to the CIXSD asking for information about the identification of an event kept by the medical records system on the patient on a given day. The CIXSD knows the patient identifications for the patient in each system and can thus send an intelligent query to the medical records system to access the needed data to be returned to the billing system. The particular software and detailed data structure of the CIXSD is not particularly critical and well within the skill of those which knowledge in the art to complete. The CIXSD advantageously uses XML or HTML protocols to exchange data with the application systems. Many if not most current sophisticated application programs can use and transmit XML or HTML data because of the prevalence of the world wide web portion of the internet in computer communications. It is also contemplated that data exchange in this system can use the HL-7 data format commonly used by health care organizations to exchange data between computer systems.

It is also preferable if the various applications send event abstracts to the CIXSD. These abstracts can be published to the other applications that can then store the data they might need for later processing. The abstracts are sent to the CIXSD that can add the appropriate identification codes before sending the information on to the appropriate server for the various applications. In general, the CIXSD itself will update its event registry for each such abstract that it processes so that the CIXSD has a complete inventory of all events which have occurred.

Figure 3:
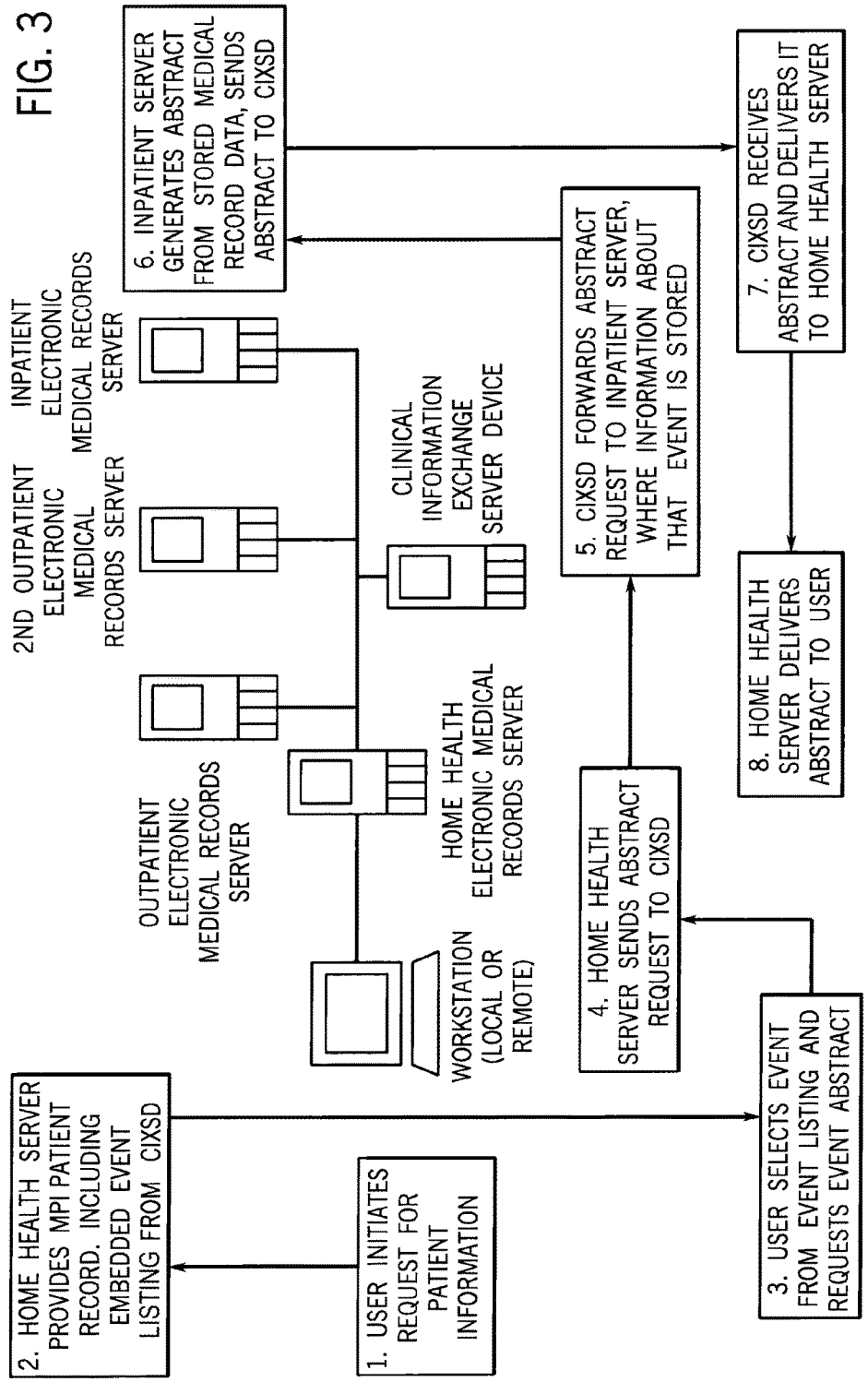
FIG. 3 is a conceptual illustration of the use of the system of the present invention.

FIG. 3 is intended to illustrate the intended functioning of the CIXSD. Four medical records application devices are indicated by the four boxes in the upper half of FIG. 3. Each device maintains and application which is maintaining its own set of data about the patient and events that involve that patient. Each application keeps identifying information about the patient using its own identification system. The CIXSD in turn collects information about the events that have been recorded by each application device. The CIXSD maintains an abstract of each such event and the abstracts are easily available to any other application in the network.

As an example, consider a home health nurse caring for a patient and using a portable computer to connect to the network of the health care enterprise. The nurse mainly uses a software application designed for home health care, but can also use the CIXSD to access abstracts of events that were originally recorded in other application systems in the network. The nurse would initially request information about the patient, as indicated at 31. The home health system application initially provides to the nurse's station a summary of the patient's medical record as indicated at 32. This summary included data from the master patient index identifying the patient and also includes an embedded event listing obtained from the CIXSD. The nurse viewing this event listing may select an event, for example a hospital stay by the patient, and request an abstract of that event, as indicated at 33. To process that request, the home health application sends a query to the CIXSD indicated at 34. The CIXSD consults the event registry and determines the date or dates of the event and determines from its own records where the information about the event is stored. The CIXSD can then send a query to the application server storing the event, using identifiers known by that application, to get the information the nurse needs, as indicated at 35. The application generates a response, perhaps just an abstract of the needed data, and sends that back to the CIXSD (at 36), which can then deliver the data to the home health system and the nurse, as indicated at 37. The nurse can view the data through a conventional web browser, as indicated at 38, if the information is transmitted and presented in XML or HTML format, or in HL-7 format. The entire communication is invisible to the user and simple seems as if all the data is directly available to the nurse through his or her computer.

Figure 4:
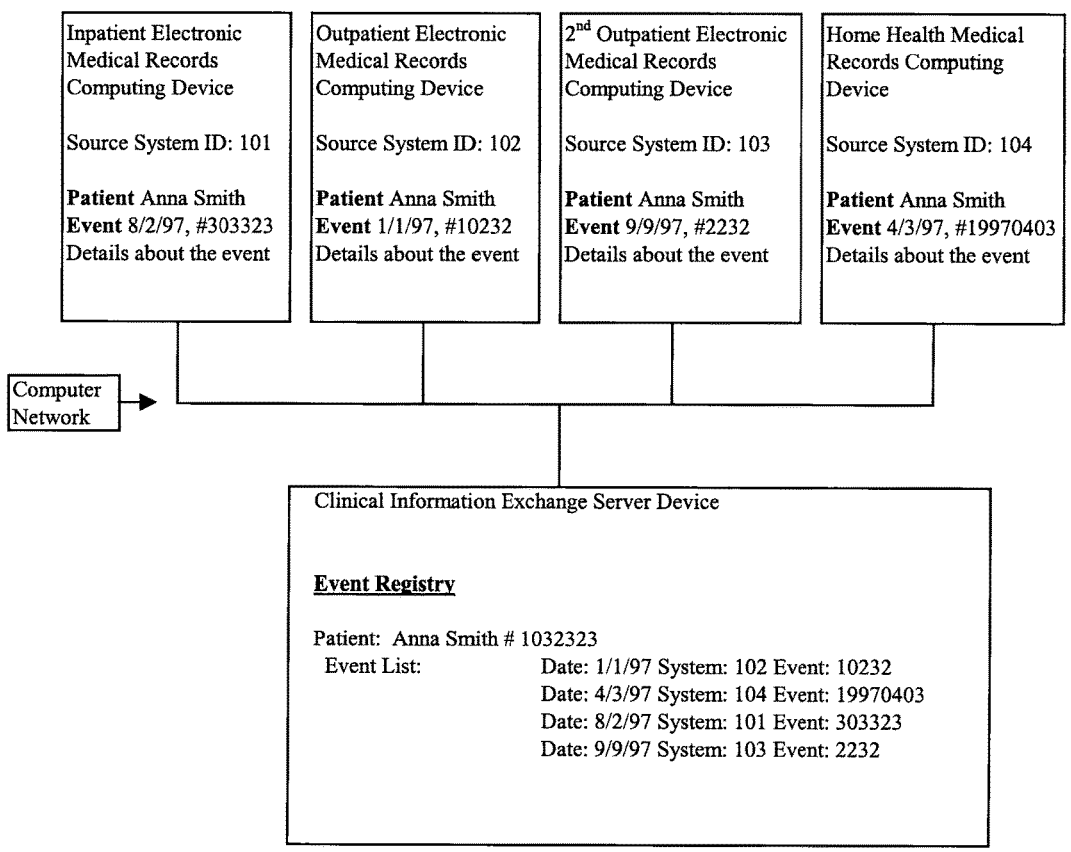
FIG. 4 is a schematic illustration of an intended use of the system of the present invention.

Shown in FIG. 4 is a diagram which is intended to illustrate the intended use of the CIXSD system. In FIG. 4, rather than illustrating the physical attributes of the data interchange, the logical connections are shown. Four systems for gathering and storing clinical data about the patient are illustrated across the top of the figure, an Inpatient Electronic Medical Records system, a first Outpatient Electronic Medical Records system, a second Outpatient Electronic Medical Records system, and a Home Health Medical Records system. It is not important if the systems are all within a common healthcare enterprise, or if they are hosted by separate but cooperating enterprises. A computer network connects each of the systems to the CIXSD server shown at the bottom of FIG. 4. The CIXSD maintains an event registry of all of the events stored by each system, lists the system holding the vent, stores the date of each event and assigns a unique event number to each event. Then each of the four systems can interrogate the CIXSD, as needed, to obtain information about events in the other systems. The CIXSD can interrogate each system in turn, to gain more data about an event in response to an inquiry from another one of the systems. In this way, each of the systems has access to the events stored by the others, yet no system needs to maintain the records or any interface information, about the other systems.

In order to implement a CIXSD system using a web based HTML protocol, two specific interfaces are preferred. The first is called GetUpdates.asp, which is a query intended to produce a list of events occurring for a particular patient. The second is called GetDetails.asp, which is a query intended to produce the details of a particular event. These merit some description. What follows is a definition of the preferred parameters of these two interfaces.

1. GetUpdates.asp
    A. Input Parameters:
        (i) Access (AccessCodes/Required)—A code used by the server to uniquely indemnify the client.
        (ii) Id (PatientID/Required)—A string that identifies the patient on the server.
        (iii) Audit (AuditRef/Required)—A string supplied by the client that can be used by the server to trace the request. This is used for audit and policy enforcement.
        (iv) RefNo (LastRefNo/Optional)—An optional numeric value the server can use to restrict the range of events returned to the client. This reference number serves as a bookmark for the last access and in optionally retuned by the query.
        (v) Days (DateRange/Optional)—This number instructs this server to return events within the past specified dates (only used if LastRefNo is not specified).
        (vi) Format (OutputFormat/Optional)—All servers are specified to return the query in HTML format. In addition, the server may support other formats (such as XML or proprietary format). Default is HTML.
    Sample Queries:
    http://Epic700/CES/update.asp?access=elctrosolor&ID=845&audit=391488588&refNo=60285
    http://Epic700/CES/update.asp?access=elctrosolor&ID=97110301&audit=3858811&days=300&format=X
    B. Returned Formats:
    If HTML return format is not specified, an HTML table is returned showing the requested events. The returned HTML page should not have <HTML> and <BODY> tags so that multiple returned pages can be concatenated together. The first row of the table has the caption of each column and does not contain patient data. Each row in the table does have:
        (i) Column 1—Date—Date of event occurrence (required).
        (ii) Column 2—Type—A short phrase of the event type (required).
        (iii) Column 3—Description—A short sentence description (optional).
        (iv) Column 4—OtherData—Other data the server may want to provide. The use of this field is for custom systems and the internal format of this filed is by agreement between the server and client (optional). It may contain information such as the provider, the clinic, the reason for the visit or any similar data.
        (v) Column 5—ReportCode—A code with which a detail report on the event may be retrieved (optional).

In addition to the table, a CIXSD may also provide the other information before and after the table. The last access reference number is returned within a tag <LastRefNo>, e.g. <LastRefNo 3051999>. Other return formats are possible and envisioned. The structure of the data can be varied. An optional standard XML return is specifically envisioned.

C. Error: If an error occurred during this query, an HTML page should be returned with the word "error" in the first line. Details of the error can be displayed in the returned HTML page. For XML, error conditions and error numbers with detailed error messages should be returned. The server should log errors for later and analysis and resolution.
    D. Logging: The client must provide an audit reference string as part of the query. This audit reference uniquely identifies the client session. Information about the user, the workstation, and the session start and end times is retrievable using the reference string for at least some period of time such as 90 days.

2. GetDetails.asp
    A. Input Parameters
        (i) AccessCode (required)—A string used by the server to uniquely identify the event.
        (ii) ReportCode (required)—A string that identifies the report event on the server.
        (iii) AuditRef (required)—A string supplied by the client that can be used by the server to trace the request. This is used for audit and policy enforcement.
    B. Returned Value: An HTML page of the report is returned.
    C. Error: If an error occurred during this query, an HTML page should be returned with the word "error" in the first line. Details of the error can be displayed in the returned HTML page. The server should log any errors for later analysis and resolution.
    D. Logging: The client must provide an audit reference string as part of the query. This audit reference uniquely identifies the client session. Information about the user, the workstation, and the session start and end time, are all retrievable using the reference string for at least some minimum period of time, such as 90 days.

The above specification of the CIXSD protocol is intended to provide an exemplar to one of skill in the art on how a CIXSD embodiment can be implemented. The protocol provides security by requiring server and client to have matching access and security codes. Each server can decide the patient information access policy of that server, the CIXSD just serving as the conduit for the request, the service of the request still being the responsibility of the application server. The two specified interface processes are implemented in HTML for maximum compatibility and to make it easy for other systems to receive and respond to CIXSD requests. Note that the provision for an audit helps to ensure accountability by allowing requests and responses to be tracked and logged.

The protocol is flexible in permitting both minimal standard (i.e. HTML) and other more custom formats for data returned in response to a query. This permits use of the protocol across diverse systems. To support the CIXSD, each server in the system must implement and support only the two defined web query interfaces describe above. Thus the burden for a new application to participate in a CIXSD enabled system is low.

It is specifically envisioned that the CIXSD capability can be implemented through a proxy. A CIXSD server can server as a proxy system for two outside system servers to request information from a common base system server. Normally in a proxy set-up, the servers acting through the proxy would act as clients only, i.e. making information requests but not responding to requests. A CIXSD server acting as a proxy would only access its data depository in the base system server, although that server could be populated with events from any other servers.

We claim:

1. In a system for distributed computing in a health care environment in which multiple different applications are in use connected on a common computer network, the improvement comprising:
at least one clinical exchange server on the network and acting as an intermediary between a plurality of different applications, each of the plurality of applications running on corresponding application servers on the network, the clinical exchange server including memory for storing data corresponding to the patients, the clinical exchange server programmed to perform the steps of:
maintaining a patient record including an event registry including data corresponding to each event recorded by the different applications the event data including:
(a) the application that recorded the event;
(b) data summarizing the event recorded by the application;
(ii) receiving a query from a first applications to identify an event in the registry corresponding to a patient, the query in a predetermined structured format comprising at least one of an XML, an HTML, and an HL-7;
(iii) using the information in the query and the data in the event registry to identify an event in the event registry corresponding to the query;
(iv) identifying an application that recorded the identified event from the data subset corresponding to the identified event;
(v) generating a second query in the predetermined structured format; and
(vi) transmitting the second query to the identified application, wherein the clinical exchange server uses the predetermined structured query comprising at least one of an XML, an HTML, and an HL-7 to transfer the event data from the server corresponding to the identified application to the first application.

2. The system as recited in claim 1, wherein the applications are affiliated with a health care service.

3. The system as recited in claim 2, wherein the health care service is selected from the group consisting of an in-patient service, an out-patient service, an ancillary service, a physical therapy service, an occupational therapy service, a scheduling service, a remote access service, and a home assistance or nursing care service.

4. The system as recited in claim 1, wherein the applications comprise at least one server.

5. The system as recited in claim 1, wherein the at least one server comprise a processor, a random access memory, and a mass storage device.

6. The system as recited in claim 5, wherein the mass storage device is selected from the group consisting of a magnetic disk and a tape drive.

7. The system as recited in claim 1, wherein the system further includes a plurality of terminals, wherein a user may use the plurality of terminals to operate the applications.

8. The system as recited in claim 7, wherein the terminals comprise a computer.

9. The system as recited in claim 1, wherein the clinical exchange server also maintains an abstract about the events sent to it to facilitate exchange of information between the applications.

10. The system as recited in claim 1, wherein the clinical exchange server also stores health insurance information about each patient, wherein the health insurance information can be accessed by any of the applications.

11. The system as recited in claim 1, wherein each patient record further includes an identification cross reference table that includes a list of applications on the network and, for each application, an application unique patient identifier used by the application wherein first and second different applications use first and second different patient identifiers for a first patient, respectively, the step of receiving a first query including receiving a query that identifies the first patient via the first patient identifier, the clinical exchange server further programmed to perform the step of using the first patient identifier to identify a first patient record associated with the first patient, the step of using the information in the first query and the event data subsets in the event registry to identify an event in the event registry associated with the first query including the step of identifying an event in the event registry of the first patient record, the clinical exchange server further programmed to perform the step of using the identification cross reference table to identify the second patient identifier, and the step of generating a second query including generating a second query that specifies the identified event and the second patient identifier.

12. The system as recited in claim 11, wherein the reference table includes a master patient index identification code assigned to the patient as well as an application specific identification number assigned to the patient by each application.

13. The system as recited in claim 11, wherein the first query includes an audit reference for tracking and logging the requests and responses.

14. The system as recited in claim 11, wherein the first query comprises a format parameter for specifying a format for returning the query.

15. The system as recited in claim 1, wherein an event comprises data corresponding to a patient encounter tracked or recorded by any of the different health care applications.

16. The system as recited in claim 1, wherein an event comprises data corresponding to at least one of a laboratory report, a chart entry, an accounting entry, and an insurance entry.

17. The system as recited in claim 1, wherein the different applications comprise at least one of an accounting system, an in-patient scheduling system, a laboratory results reporting system, a home assistance system, and a managed care system.

18. The system as recited in claim 1, wherein the different applications comprise at least one of a patient tracking application, a scheduling application, and a vendor application.

19. The system as recited in claim 1, wherein the different applications are programmed to maintain a security and an access code.

20. The system as recited in claim 1, wherein the different applications maintain a patient information access policy for the application.

* * * * *